United States Patent
Adams et al.

(10) Patent No.: US 10,098,835 B2
(45) Date of Patent: *Oct. 16, 2018

(54) PROCESS FOR MAKING CONTROLLED RELEASE MEDICAL IMPLANT AND NON-IMPLANT PRODUCTS

(71) Applicant: Robert W. Adams, Oakton, VA (US)

(72) Inventors: Robert W. Adams, Oakton, VA (US); Wayne C. Pollock, Bel Air, MD (US)

(73) Assignee: Robert W. Adams, Oakton, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/583,579

(22) Filed: May 1, 2017

(65) Prior Publication Data

US 2017/0232667 A1    Aug. 17, 2017

Related U.S. Application Data

(63) Continuation of application No. 14/429,496, filed as application No. PCT/US2013/063435 on Oct. 4, 2013, now Pat. No. 9,668,968, which is a continuation of application No. 13/796,875, filed on Mar. 12, 2013.

(60) Provisional application No. 61/709,856, filed on Oct. 4, 2012, provisional application No. 61/709,856, filed on Oct. 4, 2012.

(51) Int. Cl.

| | |
|---|---|
| *A61K 9/00* | (2006.01) |
| *A61K 31/485* | (2006.01) |
| *B33Y 10/00* | (2015.01) |
| *B33Y 80/00* | (2015.01) |
| *A61L 31/14* | (2006.01) |
| *A61L 31/16* | (2006.01) |
| *B33Y 50/02* | (2015.01) |
| *A61L 31/08* | (2006.01) |
| *B29C 64/112* | (2017.01) |
| *B29C 64/386* | (2017.01) |
| *B29K 67/00* | (2006.01) |
| *B29L 31/00* | (2006.01) |

(52) U.S. Cl.
CPC .......... *A61K 9/0024* (2013.01); *A61K 31/485* (2013.01); *A61L 31/08* (2013.01); *A61L 31/148* (2013.01); *A61L 31/16* (2013.01); *B29C 64/112* (2017.08); *B29C 64/386* (2017.08); *B33Y 10/00* (2014.12); *B33Y 50/02* (2014.12); *B33Y 80/00* (2014.12); *A61L 2300/604* (2013.01); *A61L 2420/02* (2013.01); *B29K 2067/046* (2013.01); *B29K 2995/006* (2013.01); *B29K 2995/0056* (2013.01); *B29L 2031/753* (2013.01)

(58) Field of Classification Search
CPC ...... B33Y 10/00; B33Y 80/00; A61K 31/485; A61K 9/0024; A61L 2300/604; A61L 2420/02; A61L 31/148; A61L 31/16; B29K 2067/046; B29K 2995/0056; B29L 2031/753

See application file for complete search history.

(56) References Cited

U.S. PATENT DOCUMENTS

| | | | |
|---|---|---|---|
| 5,490,962 A | 2/1996 | Cima et al. | |
| 5,633,000 A | 5/1997 | Grossman et al. | |
| 5,858,388 A | 1/1999 | Grossman et al. | |
| 6,126,956 A | 10/2000 | Grossman et al. | |
| 6,280,771 B1 | 8/2001 | Monkhouse et al. | |
| 7,169,183 B2 | 1/2007 | Liu et al. | |
| 7,276,252 B2 | 10/2007 | Payumo et al. | |
| 7,820,201 B2 | 10/2010 | Pryce Lewis et al. | |
| 8,449,901 B2 | 5/2013 | Shanley et al. | |
| 2001/0029351 A1 | 10/2001 | Falotico et al. | |
| 2002/0007294 A1 | 1/2002 | Bradbury et al. | |
| 2002/0015728 A1 | 2/2002 | Payumo et al. | |
| 2003/0198677 A1* | 10/2003 | Pryce Lewis | A61J 3/10 424/471 |
| 2004/0166140 A1 | 8/2004 | Santini et al. | |
| 2010/0303883 A1 | 12/2010 | Pollock et al. | |
| 2011/0244010 A1 | 10/2011 | Doshi | |

(Continued)

FOREIGN PATENT DOCUMENTS

CN     1732899 A     2/2006

OTHER PUBLICATIONS

Weigang et al., "The Controlled Releasing Drug Implant based on Three Dimensional Printing Technology: Fabrication and Properties of Drug Releasing in vivo" Journal of Wuhan University of Technology-Mater, Sci Ed., Dec. 2009 : 977-981p.

(Continued)

*Primary Examiner* — Robert A Wax
*Assistant Examiner* — Olga V Tcherkasskaya
(74) *Attorney, Agent, or Firm* — Novick, Kim & Lee, PLLC; Sang Ho Lee

(57) ABSTRACT

A multi-step method of making a mammalian subcutaneous medical implant or non-implant for releasing self-contained drugs on a controlled basis over at least a 3 day period includes depositing at least portions of one or more individual layers of the implant by at least one computer controlled 3-D printer. The 3-D printing method may be accomplished via an array of 3-D nozzles that deposit materials (such as plastics, thermoplastics, coating materials, drug-containing matrix materials, non-drug containing matrix materials, bonding materials, biodegradable materials and/or the like) in very small, precise portions. The materials may be deposited in liquid, powder, sheet or other forms. Non-implant forms may also be provided by the techniques disclosed herein.

6 Claims, 4 Drawing Sheets

(56) References Cited

U.S. PATENT DOCUMENTS

| | | |
|---|---|---|
| 2012/0034306 A1 | 2/2012 | Pollock et al. |
| 2013/0236524 A1 | 9/2013 | Holl et al. |
| 2015/0005595 A1 | 1/2015 | Tepper et al. |
| 2015/0165690 A1 | 6/2015 | Tow |

OTHER PUBLICATIONS

Deng Guang Yu et al., "Three-Dimensional Printing in Pharmaceutics: Promises and Problems", Journal of Pharmaceutical Sciences, vol. 97, No. 9, pp. 3666-3690 (Sep. 2008).

* cited by examiner

PROCESS FOR MAKING CONTROLLED RELEASE MEDICAL IMPLANT AND NON-IMPLANT PRODUCTS

CROSS-REFERENCE TO RELATED PATENTS AND APPLICATIONS

This is a continuation application based on U.S. application Ser. No. 14/429,496 filed on Mar. 19, 2015, which is a national-stage entry under 35 USC § 371 of PCT/US2013/063435 filed on Oct. 4, 2013, and claims the priority benefits from U.S. non-provisional patent application Ser. No. 13/796,875 filed on Mar. 12, 2013, and provisional patent application No. 61/709,856, filed on Oct. 4, 2012, the entire contents of which are hereby expressly incorporated herein by reference.

Axxia Pharmaceuticals LLC ("Axxia") owns prior issued U.S. Pat. Nos. 5,633,000; 5,858,388; and 6,126,956 and U.S. Ser. Nos. 12/738,113; 61/533,131; 13/264,813; 13/606,795; and 2008/011908, the entire contents of each such prior-issue US patent and pending patent application commonly owned by Axxia being expressly incorporated herein by reference. These Axxia prior patents and applications relate to controlled release medical implant products and various non-3-D printing processes for making those products. According to these Axxia prior patents and applications, the implants (i) may be non-biodegradable or biodegradable; (ii) may provide drug delivery over a few days, weeks or months; (iii) may provide a steady drug release without a "burst"; and (iv) may be in various sizes to accommodate the desired drug delivery schedules. Significantly, none of these prior Axxia patents or patent applications teach or suggest a 3-D printing method, let alone the 3-D printing method of this invention.

FIELD

This application sets forth novel 3-D printing processes for making subcutaneous medical implant products that provide for the controlled release of non-narcotic as well as opiate, opioid and/or other narcotic drugs over a period of days, weeks or months. These novel processes can be used to make a wide variety of subcutaneous medical implant products having self-contained controlled release drugs beyond those specifically disclosed in Axxia's prior patents and applications. The present invention covers both the 3-D printing processes described below and the products made by those processes.

Although the present invention is primarily described herein with respect to medical implant products, the invention also is applicable with respect to medical non-implant products, such as tablets having time release capabilities and/or containing opioid products. Thus, for example, the detailed description of the processes and products set forth herein with respect to implants are readily adaptable to non-implant products as would be readily understood by one of ordinary skill in the art after reading this disclosure.

Further, the drug and non-drug materials in the present invention are not limited to the materials disclosed in the Axxia patents and applications—e.g., there is no limitation to the hydromorphone drug or to the ethylene-vinyl acetate (EVA), thermoplastic polyurethane (TPU) or silicone coating/matrix materials. For example, the drug materials may be narcotics and/or non-narcotics. Likewise, the non-drug materials may be biodegradable or non-biodegradable.

Thus, in addition to hydromorphone, this process also can be used to make the probuphine implants of Titan Pharmaceuticals, the implants of Purdue Pharma and the implants products of other companies. See, e.g., U.S. Pat. Nos. 8,114,383 and 8,309,060. In other words, this application covers all subcutaneous medical implant products containing controlled release drugs that are capable of being made by the invention.

The present processes and the products made by those processes are useful in at least four fields of use: (1) the narcotic abuse field; (2) the drug compliance field (both narcotic and non-narcotic drugs); (3) the pain management field; and (4) the animal heath field.

BACKGROUND

Inkjet and other printing processes have been used in many fields to manufacture products. For example, inkjet printing processes have been used in the manufacture of LCD and semiconductor products. See, e.g., U.S. Reissue Pat. No. 37,682, which although it involves an unrelated technical field is incorporated by reference herein in its entirety.

In addition, printing processes (such as screen printing and low temperature casting techniques) have been the subject of consideration for the manufacture of other medical (non-implant medical devices or non-self-containing drug implants) products. See, e.g., "Printing Evolves: An Inkjet For Living Tissue," published in the Wall Street Journal on Sep. 18, 2012 at pages D1 and D3; and the Axxia patents/applications.

Further, non-printing methods have been used to create medical implant products, via conventional methods. These non-printing methods include, inter alia, hot-melt casting, extrusion, shrink-wrap and solvent based processes.

While some prior art processes have commercial advantages and they can be used as a part of the invention herein, it is the inventors' opinion that these prior art processes alone (i.e., when used without at least one 3-D printing process step) fail to satisfy at least one or more of the advantages that the present 3-D printing invention seeks to provide for controlled release subcutaneous medical implant devices and medical non-implant products. For example, a partial listing of the advantages that may result from the present 3-D printing invention are believed to include at least some of the following:

1. The structure of the non-drug portions of the implant or non-implant product may be designed and controlled rather precisely due to (i) the small, precise amounts of material deposited by each 3-D nozzle and (ii) the very thin or ultra-thin layer-by-layer building method of 3-D printing; and 2. The drug release pattern of the implants or non-implants may be precisely regulated by the use of the 3-D nozzles to create the product on a layer-by-layer basis for the same reasons; and 3. The shape and configuration of the implant or non-implant may be modified as desired by, for example, using the 3-D printing nozzles to deposit non-permanent materials that may be readily removed by etching, laser, mechanical, chemical or other known means; and 4. The present invention may avoid irregularities resulting from cutting or otherwise modifying extruded materials; and 5. The present invention may sometimes avoid the separate step of loading a drug material within the implant or non-implant because, for example, the precise ratio of the drug material and the non-drug material in the matrix core can be precisely regulated and the release path and release rate of the drug materials within the matrix core to the opening in the implant or non-implant device can be precisely designed; and 6. The present invention may provide great flexibility in the choice and use of both drug materials and non-drug materials, whereas, for example, certain previously known processes limit the commercial choice of plastic/thermoplastic/drug materials; and 7. Large numbers of implants or non-implants may be created at one time and/or quickly so that, e.g., the overall yield is increased; and 8. The present invention may provide improved bonding/adhesion between the drug containing matrix and other portions of the implant or non-implant (e.g. the coating); and 9. High manufacturing yield may be achieved—e.g., approaching as high as about 90-95%. Thus, for example, with hydromorphone costs of approximately $12,000/kg, this may be an important competitive advantage, especially in developing world markets. However, it should be understood that the present invention does not require that all of these advantages be achieved in every process or product covered by the scope and spirit of the invention.

SUMMARY

In general, the present invention relates to computer-controlled 3-D printing methods that are used (either wholly or in part) to manufacture controlled release medical implant or non-implant products. One type of 3-D printing is sometimes referred to as fused deposition modeling (FDM). This invention is not limited to any one type of 3-D printing. Further, and indicated previously, this invention covers both implant and non-implant processes and products. For the purpose of providing a detailed description of the invention, that description will focus upon implant processes and products. However, those processes also are applicable to the manufacture of non-implant products as would be readily understood by one of ordinary skill in the art after reviewing that description.

These subcutaneous implants provide for the controlled release of self-contained drugs (whether they are narcotic or non-narcotic drugs) over at least a several week period. In one embodiment of the invention, the controlled release time period is 30 days or longer. However, the controlled release period may, in fact, also be a shorter period of time, such as 3, 7, 14 or 21 days. Although a steady controlled release is frequently desired, the release rate can be varied over time. In addition, more than one drug may be released by an implant made in accordance with the invention.

The 3-D printing method may be accomplished via an array of 3-D nozzles that deposit materials (such as plastics, thermoplastics, coating materials, drug-containing matrix materials, non-drug containing matrix materials, bonding materials, biodegradable materials and/or the like) in very small, precise portions. The materials may be deposited in liquid, powder, sheet or other forms.

For example, the array of nozzles may be used to deposit one or more of these materials on a thin or ultra-thin layer-by-layer basis to create/build the final controlled release medical implant product. Although the 3-D nozzles may deposit the materials in droplet form, the use of the nozzle array typically will result in a non-droplet shape at each layer/slice. In one embodiment, there is a separate array of 3-D nozzles for at least one portion of each layer.

However, the number of separate arrays of 3-D nozzles may be minimized so long as the 3-D nozzles are capable of depositing more than one type of material at different times during the process. Because this presently may be commercially impractical with respect to some materials, it may not always be a preferred process feature. Nevertheless, the scope of the invention cannot be avoided by this modification.

With respect to the manufacture of the Axxia products disclosed in its prior patents and applications, the array of 3-D nozzles of this invention is capable of depositing one or more types of materials during at least a portion of at least one layer-by-layer step in the product building process. The number of different types of materials deposited by the array during any one layer deposition is dependent upon, inter alia, the composition and the geometric design of the final product. Where more than one material is deposited on a particular layer, the different materials may be deposited simultaneously (either as a mixture or by separate nozzles) or sequentially.

If deposited sequentially, a portion of the previously deposited materials in that layer may be removed prior to the subsequent deposition of other materials by techniques such as etching, lasers or other means that are well known. This removal method may be beneficial with respect to the deposition of drug materials and/or the creation of openings in the implant product.

In addition, the removed portions may involve one or more layers of other materials so that an open shell of coating materials may be created into which a drug-containing matrix core may be deposited via 3-D or other methods. In that situation, for example, a drug-containing matrix core may be deposited layer-by-layer via 3-D printing within the open shell of the outside coating structure prior to the deposition of the top coating layer(s) of the implant product. In that situation, the matrix core may be created, inter alia, by having one or more 3-D nozzles (i) deposit a mixture of the drug and non-drug materials; (ii) separately deposit the drug and non-drug materials; or (iii) deposit ultra-high pressure carbon dioxide as a part of the non-drug materials in order to create an in situ foaming material that may enhance interconnective microporosity. The drug/non-drug material may be mixed homogeneously or non-homogeneously.

Alternatively, instead of creating the matrix core within the open shell of coating materials, the matrix core may be created separately and then mechanically or otherwise inserted within the open shell.

Furthermore, the matrix core structure and/or its drug release pattern may be enhanced (with respect to one or more of the layer-by-layer depositions) by first depositing only the non-drug containing material, then removing portions of that material and then depositing the drug containing material. In that circumstance, the matrix core material and/or the opening material may be deposited sequentially. For example, one or both of these materials may be deposited after another interim or temporary material has been deposited and then removed. This approach has the potential advantage of more precisely controlling the narcotic drug release pattern via micro-channels within the matrix core and the opening in the implant device.

In yet another embodiment of the invention, a rapidly biodegradable material may be used to form all or part of the opening in the implant device. This may have the advantage of an improved hygienic product and/or to control the initial drug burst if, for example, one wanted to begin drug release several days after implantation.

Similarly, a biodegradable material may be used to form all or part of the implant which, for example, obviates the need to physically remove the spent implant. Further, biodegradable material may be used to form all or part of the non-drug portion of the core. This may serve to improve the control release of the drug materials from the core.

The present invention also contemplates a high-speed and cost-efficient 3-D printing-based manufacturing process for building incremental components into finished drug delivery implant platforms. This process involves multiple pass or sequential deposition of the same or different functional materials including active pharmaceutical ingredients wherein at least portions of some or all layers can be brought to a final physical product state using ultraviolet (UV) radiation or using other means.

More specifically, this radiation may instantly cross link the functional layers without the need for thermal assist, thereby allowing for high speed operations while eliminating the possibility of thermal decomposition to the component materials. In that regard, UV curing systems are small, portable, highly efficient and inexpensive compared to thermal curing or drying ovens. UV cross linkable formulations are 100% solids liquids going into the printing process. No solvent is necessarily required so there is no need to incur the expense of recovering or burning such a process aide that ultimately doesn't become part of or add any value the final product.

In addition, the present invention contemplates the situations where (a) the process involves the use of a 3-D printing process alone or (b) in combination with (i) an non-3-D inkjet process, (ii) a non-inkjet process, (iii) a combination of those two processes or (iv) a combination of one or more of those processes with one or more other non-printing processes (such as extrusion). For example, in the combination situation, it may be preferable to use an inkjet printer process to deposit certain materials and to use a non-inkjet printer process (or a non-printing process) to deposit other materials.

As indicated above, the present invention covers the situation where the 3-D printing method is used to create all or only a portion of the controlled release medical implant product. As a result, the invention contemplates the situation where one or more layers or where one or more parts of layers are created by non-3-D methods. For example, all or part of the matrix core may be created via 3-D printing with all or part of the core, coating and/or opening created by other processes.

Further, it should be understood that the process may be used to deposit multiple layers having the same or different thicknesses. In that regard, the dimensions of medical implant devices can vary widely, However, the implant device envisioned by this invention may be about the size of a shirt button or smaller. Thus, very approximate dimensions are about 0.5 mm to 25 mm in height and about 3 mm to 130 mm in length/diameter. Nevertheless, in the case of a large patient (e.g., a horse), the dimensions in height and/or length/diameter may be much larger. See, e.g., the discussion of the effects of these dimensions as set forth in the aforesaid Axxia prior patents and patent applications.

In addition, 3-D printing may be used to create radio opaque markers (as very generally described in Axxia prior patent application Ser. No. 2008/011908).

By utilizing the present 3-D invention, the thickness of an individual layer deposited via a 3-D printing machine can be as thin as about 0.01 mm or less. Examples of commercially available industrial 3-D printing equipment and software can be readily obtained via the Internet. See, for example, the websites of Stratasys, Organo Holdings, 3D Systems, Fortus, Daussault Systems, Autodesk and others.

The present invention is not limited to any specific 3-D printing machine or software. In other words, there is no preferred 3-D equipment or software.

By way of example only and with respect to the only ultimate products disclosed in the Axxia prior patents/applications identified above, the implant has an impermeable outer coating that surrounds a drug/non-drug matrix core. After implantation, the drug material is released on a controlled basis through one or more openings in the coating material to the mammalian (human or animal) patient.

As a result, one layer of the present implant may contain only one type of material (e.g., a coating material) as well as an opening. However, another layer of the present implant may contain multiple types of material (e.g., coating, EVA or TPU, and drug materials) as well as an opening.

In other words, the process of the present invention may be used to create not only the core (the interior drug containing matrix material) of the implant described in the Axxia patents/applications but also the openings and/or the micro-channels within the core that in combination facilitate release of the drug from the matrix core into one or more openings which lead to the exterior of the implant and from which the drug is released.

It is believed that one potentially important feature of the present process may be the creation of a strong or an improved bond (via chemical, mechanical and/or other means) between the coating and the matrix core materials. Thus, for example, a separate bonding material can be used between the outside coating material and the matrix core.

Alternatively, a very thin or ultra thin layer or portion of a layer composed of the coating material and the non-drug containing matrix material may be formed via 3-D printing (either simultaneously or sequentially). These materials can be separated deposited via different nozzles or they can be deposited together as a mixture via the nozzles. This may result in a strong or an improved bond.

DETAILED DESCRIPTION

The present invention covers a wide variety of 3-D printing processes that may be used to create virtually any implant or non-implant device. Therefore, the selection and description of a particular implant/non-implant device or a particular 3-D process for illustrative purposes is not intended to limit the scope of the invention.

Figure 1:
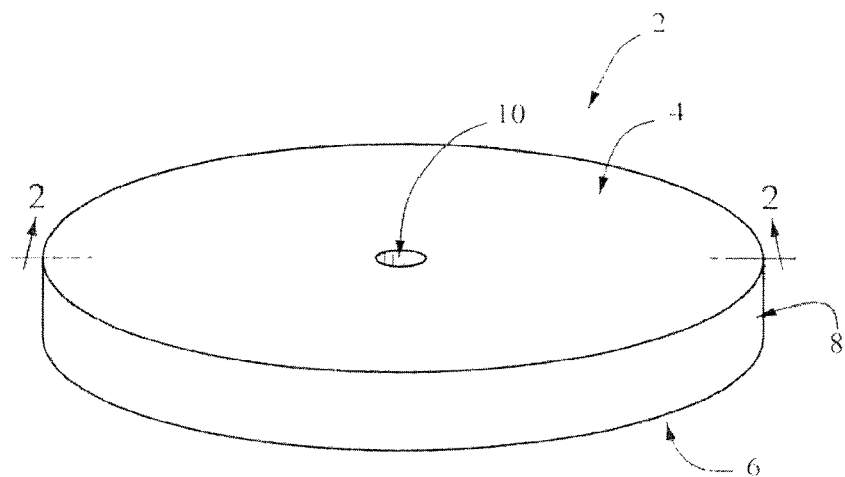
FIG. 1 is a perspective view of an exemplary embodiment of a product made by the process of the present invention. The size and dimensions of the product have been exaggerated for illustrative purposes.
Figure 2:
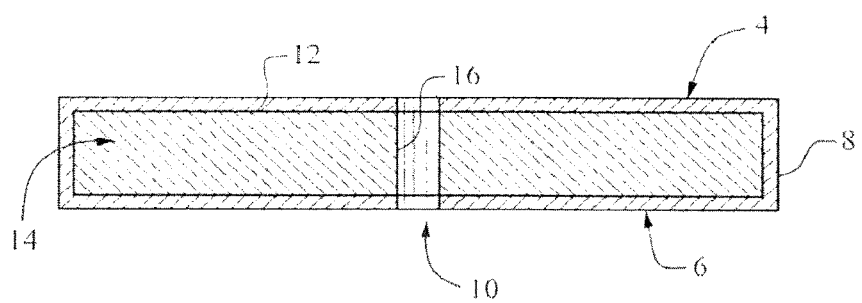
FIG. 2 is a cross-sectional view of the product in FIG. 1 along line 2-2. The size and dimensions of the product have been exaggerated for illustrative purposes.

In that regard, the implant device in FIGS. 1 and 2 is prior art, see Axxia U.S. Pat. No. 6,126,956. That implant structure is used solely for illustrative purposes and it is not intended to limit the scope of this invention because the invention covers any implant device manufactured in whole or in part via a 3-D printing process.

Turning to FIG. 1, an abuse deterrent, subcutaneous implant 2 permits the controlled release of self-contained drug materials. A self-contained drug implant means that all of the drug materials are within the implant prior to being implanted into the patient. The phrase is intended to distinguish medical devices (such as a pump) wherein additional drugs are introduced into the patient via the device after the device has been implanted into the patient.

Implant 2 typically will have a top 4, a bottom 6 and an outside wall 8. Although FIG. 1 illustrates implant 2 in a button-like or cylindrical shape, virtually any geometric shape can be constructed, if desired. An opening 10 permits the controlled release of the drug—whether a narcotic or non-narcotic drug.

Although FIG. 1 shows one opening 10, it also is possible that one or more openings could be used with respect to an implant containing more than one drug having different release rates. Typically, however, one opening can be used with respect to the release of more than one drug. See FIG. 5 discussed below.

In addition, all or part of opening 10 may contain removable materials. For example, the opening may contain rapidly biodegradable substances so that the opening is not complete until after insertion into the human or animal at which time this rapidly biodegradable material will be absorbed or will otherwise disappear in the human or animal. Examples of such a rapidly biodegradable material include, inter alia, "Biodegradable Polymer Implants to Treat Brain Tumors," Journal of Controlled Release 74 (2001) 63-67; and "An Introduction to Biodegradable Polymers as Implant Materials," White Paper from Inion OY (2005).

If a rapidly biodegradable material is used to create temporary plugs at the portions of the opening 16 at and near the top and the bottom of implant 2 it may be desirable to fill the remainder of the opening with a different rapidly biodegradable material, such as water or saline. In that situation, the plug portion of the rapidly biodegradable material may be selected from suitable materials so that the plug will rapidly degrade after implantation—but not during normal production, transportation or handling.

Of course, alternatively the opening may be filled with non-biodegradable materials in during the 3-D manufacturing process so long those materials are removed prior to being implanted in the patient.

FIG. 2, shows the cross-sectional view of the product in FIG. 1 along line 2-2. The top, bottom and side walls create an impermeable coating 12. Within coating 12, is a controlled release matrix core 14 containing both drug and non-drug material. By virtue of 3-D printing the structure of this matrix core and its release pattern may be controlled very precisely. Matrix core 14 has an uncoated wall 16 within implant 2 that abuts opening 10 in order to permit the desired controlled release of the drug to the patient.

Coating 12 may be made up of one or more materials. Some examples of coating materials include, but are not limited to, polymers, plastics, thermoplastics, EVA, TPU and silicone.

Coating 12 should be impermeable in at least two ways. First, it must be impermeable in terms of prohibiting the flow of the drug material from the matrix core 14 other than via designed openings.

Second, it must be impermeable in the sense that it has a high breaking strength. U.S. Pat. No. 8,114,383 indicates that the breaking strength should be at least 500 N. However, it is believed that a lower breaking strength (such as about 250 N) is still sufficiently high so as to be commercially acceptable.

In addition, the present invention also contemplates the optional use of a bonding material between coating 12 and matrix core 14. These bonding materials are well known and they are preferably chosen on the basis of the coating and core materials.

If the coating and non-drug matrix core materials consist of EVA, TPU and/or silicone, any suitable materials may be selected. Further, the bonding material may be created from a mixture of the coating material and the matrix core material.

If the bonding material is sufficiently impermeable, then coating 12 need not be impermeable.

As described above, matrix core 14 contains both a drug and non-drug material. In the drug abuse field, the drug will involve a narcotic, See, U.S. Pat. No. 8,114,383, col. 2, 1. 45 to col. 5, 1. 32 for a partial listing of narcotic drugs.

In the drug compliance, pain management and animal health fields, the drug may be narcotic and/or non-narcotic.

The currently preferred process involves the use of just 3-D printing methods (but it does not exclude the use of some non-3-D printing steps). Thus, FIGS. 3A to 3E illustrate only a 3-D printer process for the manufacture of medical implant devices.

Figure 3A:
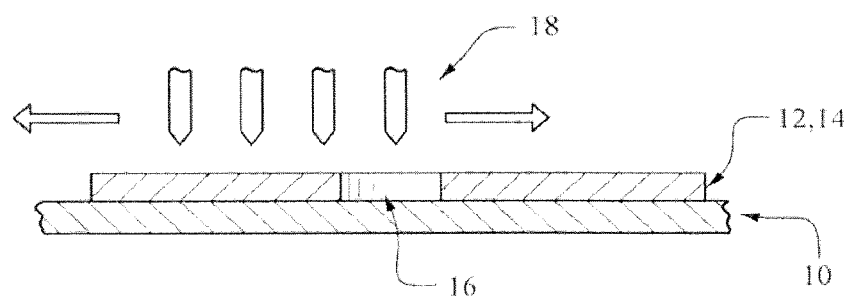
FIGS. 3A, 3B, 3C, 3D and 3E illustrate in cross-sectional, partial views along line 2-2 some (but not necessarily all) of the processing steps required to fabricate the products of FIGS. 1 and 2. Once again, the size and dimensions have been exaggerated for illustrative purposes. In addition, the size, location and number of 3-D printing nozzles have been exaggerated for illustrative purposes.

FIG. 3A illustrates the first step in the preferred embodiment of the 3-D printing process. In this preferred embodiment, the entire implant 2 is built solely via 3-D printing. However, as described above, the present invention only requires that at least a portion of one layer of the implant device be made via 3-D printing. Thus, the invention covers the use of a 3-D printing process with other processes for making an implant.

Stage 10 is the product building platform upon which the medical implant 2 device will be built via a very thin or ultra thin layer-by-layer 3-D printing deposition process. As currently envisioned, there will be at least three layer-by-layer depositions.

Stage 10 may be stationary. If stage 10 is stationary, then one 3-D process design involves the use of multiple arrays of nozzles for the layer-by-layer deposition of materials. In that situation, the stationary product building stage 10 utilizes multiple movable arrays of nozzles capable of depositing each layer or a portion of each layer. Thus, each separate array of nozzles can be designed to deposit one or more layers of materials for building the implant device.

Although it is conceivable that a single array of nozzles can be used to deposit different materials via one or more of the nozzles in that single array, it is presently contemplated that the use of multiple arrays of nozzles will be more commercially acceptable in terms, for example, of the potential problems that may arise where more than one material is deposited by an individual nozzle at various layer steps of the layer-by-layer building process.

Currently, a non-stationary stage 10 is preferred. In that situation, the product may be built layer-by-layer by moving it along a path having more than one array of nozzles. This product building path may consist of one chamber or more than one chamber, To ensure a high degree of product purity, the use of multiple "clean" chambers may be desirable. Thus, for example, a separate chamber may be desired for (a) the layer-by-layer construction of the bottom coating/opening/coating layer, (b) the layer-by-layer construction of the coating/core/opening/core/coating layer and (c) the layer-by-layer construction of the top coating/opening/coating layer.

Further, separate chambers may be desirable with respect to the optional bonding layers between (i) the top layer of the bottom coating and the bottom layer of the matrix core and (ii) the bottom layer of the top coating and the top layer of the matrix core. See FIGS. 3B and 3D.

FIG. 3A also illustrates a bottom coating layer 12 of the implant 2 device being deposited on stage 10. Bottom coating layer 12 contains one or more impermeable coating materials 14. In addition, this layer contains an opening 16 or opening materials (that will later be removed in whole or in part to create an opening during manufacture). In the preferred embodiment, bottom coating layer 12 is created via an array of 3-D printing nozzles 18, only some of which are illustrated in FIG. 3A.

As indicated above, the size of the controlled release medical implant 2 can vary. For example, the implants may be the size of a shirt button or smaller. However, the implants may be larger, depending upon the particular application, the desired controlled release rate and/or the size of the patient (e.g., a large horse).

The use of a 3-D printing method permits a considerable variation in the thickness of the materials being deposited on a specific layer and it also permits considerable variation in thickness of the various layers being deposited. Thus, for example, on the very first layer-by-layer deposition shown in FIG. 3A, bottom coating layer 12 has one thickness and opening 16 has no thickness.

Similarly, bottom coating layer 12 can be built in one or more layer-by-layer depositions. If there is more than one such deposition, the depositions may be of the same or different thicknesses. If more than one layer is deposited, then the choice of coating materials and their composition % may vary.

Figure 3B:
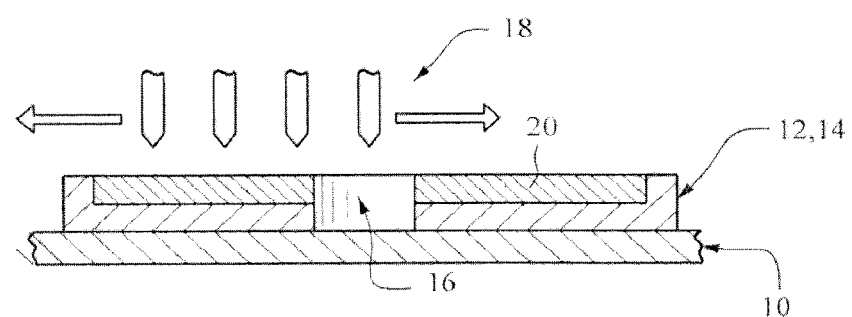

FIG. 3B illustrates the situation where one or more layers of coating 12 have been deposited so that the desired thickness of the coating material has been achieved. FIG. 3B also illustrates the next different process step wherein an optional bonding layer 20 is deposited.

Although bonding layer 20 may be a single material that is different from the coating material 12 or the matrix core material, FIG. 3 illustrates the situation, where the bonding layer is composed of the coating material and the matrix core material. More specifically, in this preferred embodiment, the bonding material is a mixture of the coating material 14 and the non-drug matrix core material. FIG. 3B shows this mixture being deposited simultaneously via 3-D printer nozzles. However, it also is contemplated that the nozzles 18 may deposit the coating and matrix core materials separately (either at the same time or sequentially).

Alternatively, the bonding material may be composed, in whole or in part, of different materials so long as the bonding material ensures sufficient adhesion between the coating materials 14 and the matrix core materials.

As with all of the layers in this process, the thickness of the bonding material layer may be varied depending upon the design requirements of the implant 2 device. FIG. 3B illustrates the deposition of only one layer of bonding materials. However, more than one layer may be utilized. If more than one layer is deposited, then the choice of bonding materials and their composition % may vary.

Figure 3C:
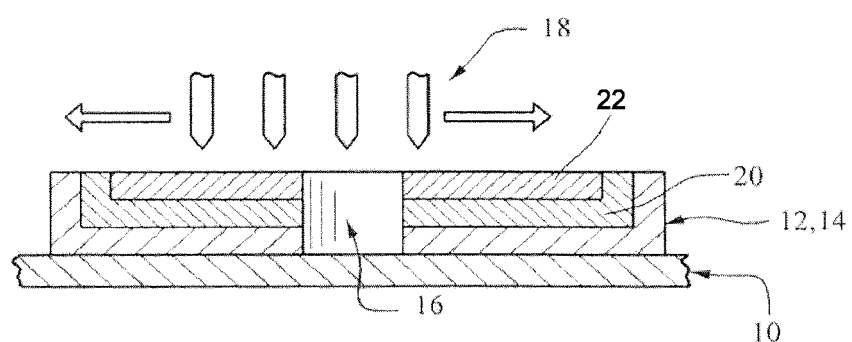

FIG. 3C illustrates the deposition of the first layer of the matrix core 22. The matrix core 22 is made from the matrix core materials that are selected when designing the composition and structure of the implant 2. In the preferred embodiment, the matrix core materials are deposited via 3-D nozzles 18 in the form of a mixture of drug and non-drug materials (as, for example, described in the mixture of materials disclosed in Axxia's prior patents and applications). The particular % composition of this mixture can be varied to meet the desired specifications for the implant 2. Further, these materials may be deposited homogenously or non-homogeneously depending upon the design of the desired micro-channels.

However, it also is envisioned that the drug and non-drug materials forming the matrix core may be deposited separately via nozzles 18 that deposit only one of these materials. The overall matrix core structure of such a deposition process is believed to provide potentially enhanced drug release profiles because specifically defined micro-channels can be designed via such a deposition process.

FIG. 3C also shows optional bonding layer 20.

Figure 3D:
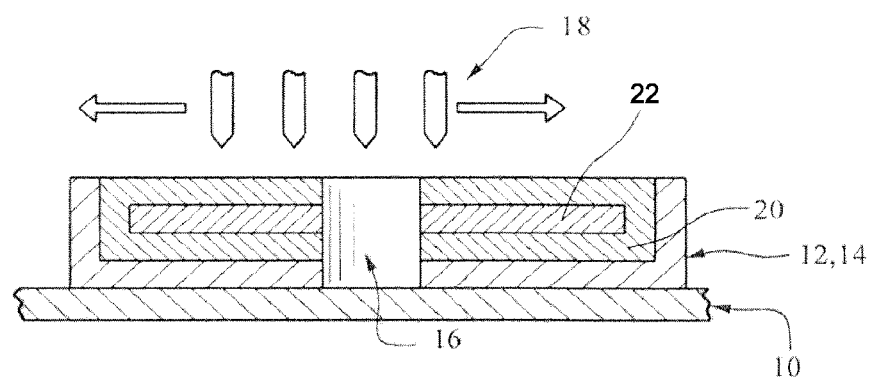

FIG. 3D illustrates the situation where one or more layers matrix core materials have been deposited so that the desired thickness of the matrix core 22 has been achieved. FIG. 3D also illustrates the next different process step wherein another optional bonding layer 20 is deposited. The comments with respect to FIG. 3B are generally applicable here.

FIG. 3D shows where optional bonding layer 20 is being deposited via 3-D printer nozzles. As a result, optional bonding layer 20 surrounds the matrix core 22. If more than one layer is deposited, then the choice of bonding materials and their composition % may vary.

Figure 3E:
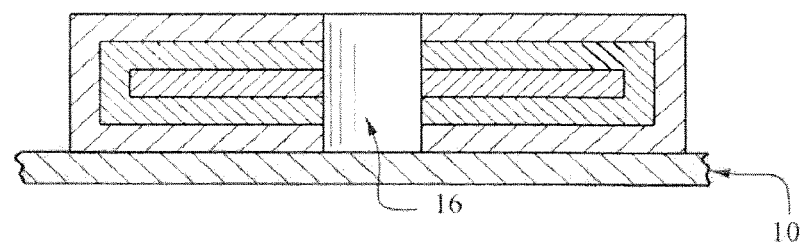

FIG. 3E illustrates the situation where one or more layers of coating material 14 have been deposited via a 3-D printing process so as to create the top portion of coating layer 12. If more than one layer is deposited, then the choice of coating materials and their composition % may vary.

As discussed above, the preferred embodiment creates an opening 16 during the manufacture of implant device 2. However, the present invention also contemplates the situation where materials are inserted into opening 16 on an interim or temporary basis during the 3-D manufacturing process. However, as explained herein, these materials will typically be entirely removed prior to implanting the device into the patient.

Thus, with respect to non-biodegradable materials, all of those materials should be removed prior to implanting via well known means such as etching, mechanical means (such as perforation or drilling), chemical means, lasers or the like. At the present time, it is the inventors' opinion that chemical means appear to be the least commercially viable because they may have the potential effect of interfering with the drug materials in the matrix core 22 and/or of interfering with the controlled drug release.

Alternatively, rapidly biodegradable materials may be utilized within the opening. These materials may be entirely removed via the means set forth above.

However, it also is envisioned that a small portion of the rapidly biodegradable materials may be left within the opening 16 so that this portion will quickly disappear after being implanted in the patient. The remaining rapidly biodegradable material may be in the form of a thin plug at the ends of the opening and/or a thin coating along the sidewalls of the opening.

In another embodiment of the invention, the outside shape of the medical implants or non-implants can be constructed by having each layer created within an existing outside mold or the like. This may be beneficial with respect to spherical, non-cylindrical and/or non-flat shapes.

Figure 4:
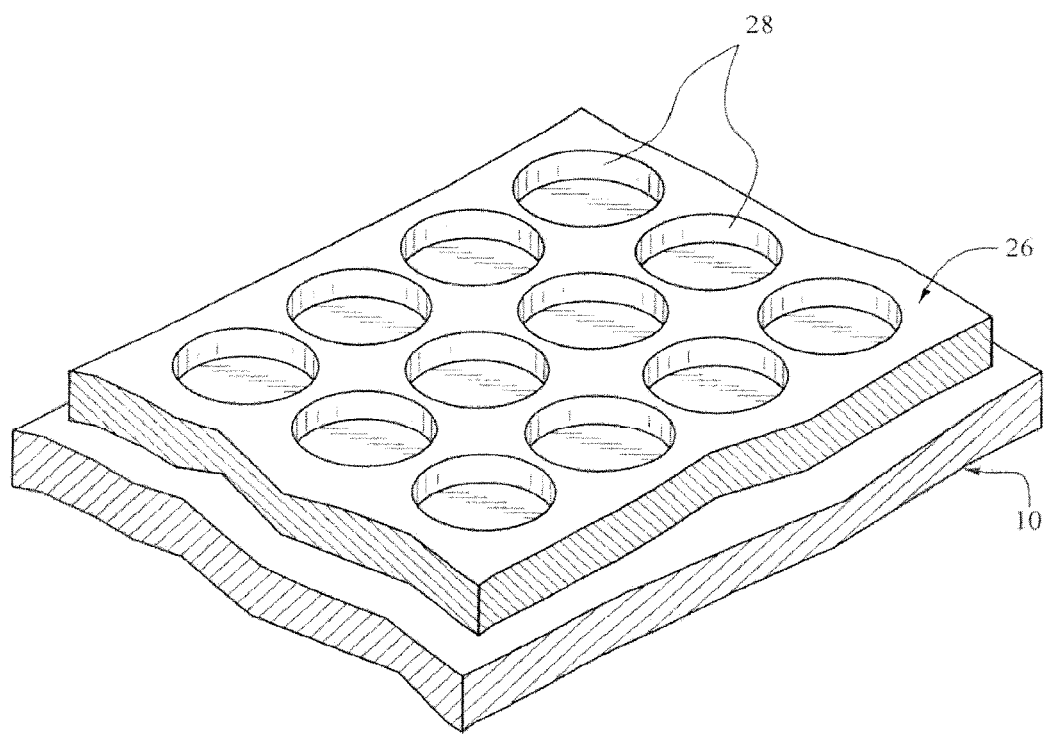
FIG. 4 illustrates the use of a mold (that can be reusable or not) to serve as the boundary between individual implant devices. The dimensions of the mold in this drawing also have been exaggerated for illustrative purposes.

FIG. 4 illustrates a situation where an outside mold 26 may be utilized to enhance the rapid production of large numbers of implants. In one example of a mold 26, a matrix mold has curved mold walls 28 that assist in building large numbers of implants.

In this preferred embodiment the mold is re-usable and an individual implant device 2 is created within the separate walls 28 of mold 26. The walls of mold 26 may be designed so that they create the appropriate shape for the implants. In addition, the walls 28 may be coating with an appropriate material so that, upon removal from stage 10, the implants are easily removed from the mold (e.g., by gravity).

Alternatively, the mold may be non-reusable. For example, a thin mold wall may be created so that it becomes a part of the implants being manufactured. Then, after 3-D processing is complete, the individual implants may separated from each other at the by using laser or other cutting means to remove all or part of the mold.

In that situation, mold 26 may be created prior to the 3-D printing process. On the other hand, it also is envisioned the nozzles 18 can be used to create/build such a non-reusable mold during the implant manufacturing process.

Thus, it is contemplated that, as with semiconductor manufacturing where large numbers of individual semiconductors are created at one time during processing, implants 12 may be created in very large numbers by the present invention. Subsequently, as described above, the individual implants may be separated by mechanical means (e.g., cutting via lasers or blade mechanisms) or by other means (e.g., via chemical etching or otherwise removing the undesired portions). Also, as described above, reusable or non-reusable matrices may be used to create large numbers of implants.

Although the preferred embodiment in FIG. 3 do not utilize any non-3-D printing steps, the present invention does not mandate that only 3-D printing steps are used to make the medical implant or non-implant devices. Instead, it only requires that a 3-D printing process is used to make at least a portion of one or more layers of the devices.

An example of this includes the situation where a sheet of the coating layer material 14 is laid upon a stage 10. See FIG. 3A. This coating material may be part or all of bottom coating layer 12. Thereafter, the implant device 12 is generally built in accordance with FIGS. 3B to 3E. Thus, where many implants are built upon this sheet of material, the individual implants may be separated from each other via laser or other means. Similarly, the openings may be created either via (a) laser or other means or (b) non-deposition in the openings area when practicing the invention.

Another example is where the matrix core material is made in whole or in part via 3-D printing. This matrix core can be embedded with a coating layer made by any number of means—such as 3-D printing, extrusion, shrink wrap, spray et cetera. Thereafter, an opening may be created by any of the means described herein or otherwise known to one of ordinary skill in the art.

In addition, it should be understood that the materials in any particular layer (e.g., the coating and matrix core layers) may vary within that layer due to the thin and very thin nature of the 3-D printing method.

Figure 5:
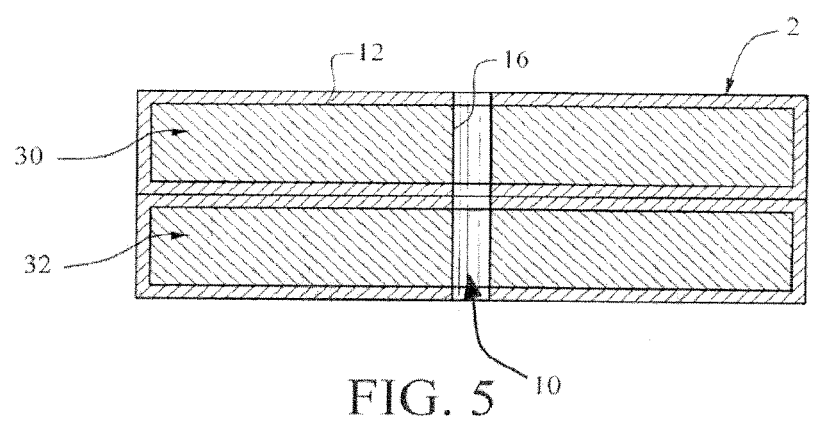
FIG. 5 illustrates the creation of an implant where more than the core contains more than one drug.

Moreover, as mentioned above, the implant may contain more than one drug. FIG. 5 illustrates one example of such an implant. This embodiment shows a "double decker" implant design. Implant 2 has a coating 12 that essentially surrounds two cores 14. Implant 2 also has an opening 19 with uncoated walls 16. In this embodiment, different drug materials 30, 32 are contained in the two cores 14. Of course, it is possible to have more than just two drugs within the implant by, for example, have more than two cores.

As may be readily appreciated by those of skill in the manufacture of medical implant or non-implant device art, the present invention can be practiced other than as is specifically disclosed herein. Thus, while the invention has been described generally and with respect to certain preferred embodiments, it is to be understood that the foregoing and other modifications and variations may be made without departing from the scope or the spirit of the invention.

The invention claimed is:

1. A multi-step method of forming a plurality of mammalian subcutaneous medical implants, each implant comprising a matrix whereby the matrix releases one or more biodegradable drugs on a controlled basis over at least a three day period, wherein the method comprises:
    supplying a prefabricated material to a first, clean depositing chamber,
    depositing one or more matrix layers of said plurality of implants directly or indirectly over said prefabricated material using at least one computer controlled 3-D printer having one or more printer nozzles within said first, clean depositing chamber;
    at least partial hardening of said deposited one or more matrix layers using non-ambient thermal or UV radiation either in said first depositing chamber or prior to a subsequent 3-D printer depositing within a second separate, clean depositing chamber;
    transporting from said first depositing chamber to said second depositing chamber the deposited one or more matrix layers of said plurality of implants over said prefabricated material,
    depositing within said second depositing chamber directly or indirectly over said transported prefabricated material one or more additional matrix layers using at least one computer controlled 3-D printer having one or more printer nozzles;
    at least partially hardening said second chamber deposited additional matrix layers using non-ambient thermal or UV radiation either within said second depositing chamber or prior to a subsequent separation of said plurality of implants;
    completing the formation of said plurality of implants; and
    separating said plurality of implants after said depositing steps so as to form a large number of said implants at the same time.

2. The method according to claim 1, wherein each implant comprises a coating that is formed at least in part by using a computer controlled 3-D printer to deposit at least a portion of one coating layer.

3. The method according to claim 1, wherein a multilayer portion of the matrices of said plurality of implants is formed solely by 3-D printers using one or more printer nozzles.

4. A multi-step method of forming a plurality of biodegradable mammalian medical non-implants, each non-implant comprising a matrix whereby each non-implant releases one or more biodegradable drugs on a controlled basis, wherein the method comprises:
    supplying a prefabricated material to a first, clean depositing chamber, depositing one or more matrix layers of said plurality of non-implants directly or indirectly over said prefabricated material using at least one computer controlled 3-D printer having one or more printer nozzles within said first, clean depositing chamber;

at least partial hardening of said deposited one or more matrix layers using non-ambient thermal or UV radiation either in said first depositing chamber or prior to a subsequent 3-D printer depositing within a second separate, clean depositing chamber;

transporting from said first depositing chamber to said second depositing chamber the deposited one or more matrix layers of said plurality of non-implants over said prefabricated material, depositing within said second depositing chamber directly or indirectly over said transported prefabricated material one or more additional matrix layers using at least one computer controlled 3-D printer having one or more printer nozzles;

at least partially hardening said second chamber deposited additional matrix layers using non-ambient thermal or UV radiation either within said second depositing chamber or prior to a subsequent separation of said plurality of non-implants;

completing the formation of said plurality of non-implants; and separating said plurality of non-implants after said depositing steps so as to form a large number of said non-implants at the same time.

5. The method according to claim 4, wherein each non-implant comprises a biodegradable coating that is formed at least in part by using a computer controlled 3-D printer to deposit at least a portion of one coating layer.

6. The method according to claim 4, wherein a multilayer portion of the matrices of said plurality of non-implants is formed solely by 3-D printers using one or more printer nozzles.

* * * * *